United States Patent [19]

Gopal

[11] Patent Number: 5,811,297

[45] Date of Patent: Sep. 22, 1998

[54] IMMORTALIZED HEMATOPOIETIC CELL LINES, CELL SYSTEM THEREOF WITH STROMAL CELLS, IN VITRO, EX VIVO AND IN VIVO USES, & IN VITRO GENERATION OF DENDRITIC CELLS AND MACROPHAGES

[75] Inventor: T. Venkat Gopal, Gaithersburg, Md.

[73] Assignee: AMBA Biosciences, LLC, Gaithersburg, Md.

[21] Appl. No.: 612,302

[22] Filed: Mar. 7, 1996

[51] Int. Cl.$^6$ ............... C12N 5/10; C12N 15/63; C12N 15/79; C12N 15/87

[52] U.S. Cl. ................. 435/320.1; 435/172.2; 435/172.3; 435/325

[58] Field of Search ............ 435/320.1, 240.1, 435/240.2, 172.2, 172.3, 325

[56] References Cited

FOREIGN PATENT DOCUMENTS

| | | |
|---|---|---|
| WO 93/18137 | 9/1993 | WIPO . |
| WO 93/20186 | 10/1993 | WIPO . |
| WO 95/09640 | 4/1995 | WIPO . |
| WO 95/11692 | 5/1995 | WIPO . |
| WO 95/14078 | 5/1995 | WIPO . |
| WO 95/31557 | 11/1995 | WIPO . |
| WO 96/02662 | 2/1996 | WIPO . |

OTHER PUBLICATIONS

Bouaboula et al., Leukemia 10:505–513 (1996).
Roux et al., Oncogene 6(11):2155–2160 (1991).
Verfaillie, C.M., "Soluble factor(s) produced by human bone marrow stroma increase cytokine–induced proliferation and maturation of primitive hematopoietic progenitors while preventing their terminal differentiation", Blood 82: 2045–2053 (1993).
Roecklein, B.A., and Torok–Strob, B., "Functionally distinct human marrow stromal cell lines immortalized by transductioin with the human papilloma virus E6/E7 genes", Blood 85: 997–1005 (1995).
Rafii, S., et al., "Human bone marrow microvascular endothelial cells support long–term proliferation and differentiation of myeloid and megakaryocytic progenitors", Blood 85:3353–3363 (1995).
Mulligan, R.C., "The basic science of gene therapy", Science 260: 926–932 (1993).
Coulombel, L., et al., "Enzymatic treatment of long–term human marrow cultures reveals the preferential location of primitive hemopoietic progenitors in the adherent layer", Blood 62: 291–297 (1983).
Berardi, A.C., et al., "Functional isolation and characterization of human hematopoietic stem cells", Science 267: 104–108 (1995).
Garcia–Bustos, J., et al., "Nuclear protein localization", Biochem. Biophys. Acta 1071: 83–101 (1991).
Raikhel, N., "Nuclear targeting in plants", Plant Physiol. 100: 1627–1632 (1992).

Citovsky, V., et al., "Nuclear localization of agrobacterium VirE2 protein in plant cells", Science 256: 1802–1805 (1992).
Sadler et al., "A Yeast gene important for protein assembly into the endoplasmic reticulum and the nucleus has homology ot DnaJ, an *Escherichia coli* heat shock protein", *J. Cell Biol.* 109: 2665–2675 (1989).
Okada, C.Y. and Rechsteiner, M., "Introduction of macromolecules into cultured mammalian cells by osmotic lysis of pinocytic vesicles", Cell 29: 33–41 (1982).
Takai, T., et al., "DNA transfection of mouse lymphoid cells by the combination of DEAE–dextran–mediated DNA uptake and osmotic shock procedure", Biochem. Biophys. Acta 1048: 105–109 (1990).
Michael, S.I., et al., "Binding–incompetent adenovirus facilitates molecular conjugate–mediated gene transfer by the receptor–mediated endocytosis pathway", J. Biol. Chem. 268: 6866–6869 (1993).
Naruyama et al., P.N.A.S. (USA) 87: 5744 (1990).
Rhim, J.S., et al., "Neoplastic transformation of human keratinocytes by polybrene–induced DNA–mediated transfer of an activated oncogene", Oncogene 4: 1403–1409 (1989).
La Thangue, N.B., "DRTF1/E2F: an expanding family of heterodimeric transcription factors implicated in cell–cycle control", Trends in Biochem. Sci. 19: 108–114 (1994).
Rafii, S., et al., "Isolation and Characterization of human bone marrow microvascular endothelial cells: hematopoietic progenitor cell adhesion", Blood 84: 10–19 (1994).
Johnson, D.G., et al., "Expression of transcription factor E2F1 induces quiescent cells to enter S phase", Nature 365: 349–352 (1993).
Singh, P., et al., "Overexpression of E2F–1 in rat embryo fibroblasts leads to neoplastic transformation", EMBO Journal 13: 3329–3338 (1994).
Caux, C., et al., "GM–CSF and TNF–$\alpha$ cooperate in the generation of dendritic Langerhans cells", Nature 360: 258–261 (1992).
Caux, C., et al., "Activation of human dendritic cells through CD40 cross–linking", J. Exp. Med. 180: 1263–1272 (1994).
Schwarzbaum, S., et al., "The generation macrophage–like cell lines by transfection with SV40 origin defective DNA", J. Immunol. 132: 1158–1162 (1984).
Cameron, P.U., et al., "Dendritic cells exposed to human immunodeficiency virus Type–1 transmit a vigorous cytopathic infection to CD4$^+$ T cells", Science 257: 383–387 (1992).

(List continued on next page.)

*Primary Examiner*—Johnny F. Railey, II
*Attorney, Agent, or Firm*—Foley & Lardner

[57] ABSTRACT

Extended life hematopoietic cell lines include stromal cell lines useful for the in vitro maintenance of undifferentiated pluripotent hematopoietic stem cells. Undifferentiated and differentiated immortalized stem cells are suitable for bone marrow transplantation, gene therapy and cell therapy applications, and as an in vitro model system for drug discovery and toxicological testing.

12 Claims, No Drawings

OTHER PUBLICATIONS

Pope, M., et al., "Conjugates of dendritic cells and memory T lymphocytes from skin facilitate productive infection with HIV–1", Cell 78: 389–398 (1994).

Berliner, N., et al., "Granulocyte colony–stimulating factor induction of normal human bone marrow progenitors results in nuetrophil–specific gene expression", Blood 85: 799–8032 (1995).

Bartley, T.D., et al., "Identification and cloning of a megakaryocyte growth and development factor that is a ligand for the cytokine receptor Mpl", Cell 77: 1117–1124 (1994).

de Sauvage, F.J., et al., "Stimulation of megakaryocytopoiesis and thrombopoiesis by the c–Mpl ligand", Nature 369: 533–538 (1994).

Lok, S., et al., "Cloning and expression of muring thrombopoietin cDNA and stimulation of platelet production in vivo", Nature 369: 565–568 (1994).

Rennick, D., et al., "Cofactors are essential for stem cell factor–dependent growth and maturation of mast cell progenitors: comparative effects of interleukin–3 (IL–3), IL–4, IL–10,and fibroblasts", Blood 85:57–65 (1995).

Graber, N., et al., "T cells bind to cytokine–activated endothelial cells via a novel, inducible sialoglycoprotein and endothelial leukocyte adhesion molecule–1", J. Immunol. 145: 819–830 (1990).

Puleo, D.A., and Huh, W.W., "Acute toxicity of metal ions in cultures of ostogenic cells derived from bone marrow stromal cells", J. Applied Biomaterials 6: 109–116 (1995).

Gandhi, G., et al., "Genotoxic effects of deltamethrin in the mouse bone marrow micronucleus assay", Mut. Res. 346: 203–206 (1995).

Bhalla, K., et al., "2'–dexoycytidine protects normal human bone marrow progenitor cells in vitro aganist the cytotoxicity of 3'–azido–3'–deoxythymidine with preservation of antiretroviral activity", Blood 74: 1923–1928 (1989).

Mackay, J.M., et al., "Trichloroacetic acid: investigation into the mechanism of chromosomal damage in the in vitro human lymphocyte cytogenetic assay and the mouse bone marrow micronucleus test", Carcinogenesis 16: 1127–1133 (1995).

Chan, T.C.K., et al., "Antiviral nucleoside toxicity in canine bone marrow progenitor cells and its relationship to drug permeation", Eur. J. Haematol. 49: 71–76 (1992).

IMMORTALIZED HEMATOPOIETIC CELL LINES, CELL SYSTEM THEREOF WITH STROMAL CELLS, IN VITRO, EX VIVO AND IN VIVO USES, & IN VITRO GENERATION OF DENDRITIC CELLS AND MACROPHAGES

BACKGROUND OF THE INVENTION

FIELD OF THE INVENTION

This invention relates to the development of certain bone marrow derived hematopoietic cell lines and their in vitro, ex vivo and in vivo uses. More specifically, this invention relates to the development of several bone marrow stromal cell lines suitable for the in vitro reconstitution of a bone marrow microenvironment capable of supporting the continuous growth of transfected hematopoietic cells derived from various sources (progenitor cells). These cells remain undifferentiated in the presence of the stromal cell lines, and undergo terminal differentiation in their absence. The progenitor cell lines can be developed into dendritic cells and macrophages under specified conditions in the absence of the stromal cell lines. These homogenous populations of hematopoietic cell lines are suitable as an in vitro model for toxicological drug testing and as a drug discovery tool.

DESCRIPTION OF THE BACKGROUND

The development of various blood cells takes place in the bone marrow. This is the main source for totipotent hematopoietic stem cells (HSCs) and progenitor cells in the mammalian adult. Totipotent HSCs remain in the bone marrow in a quiescent state at a fairly constant number throughout the life span of an individual. The mechanism for self-renewal of HSCs is poorly understood. In bone marrow, HSCs are present in close proximity to various stromal cells, and this complex milieu is presumed to play a significant role in the maintenance of the quiescent state, in the self renewal capacity and proliferation of HSCs, as well as in differentiation of hematopoietic progenitor cells. In vitro long term bone marrow culture (LTBMC) systems have been developed to study the molecular mechanisms underlying the maintenance, proliferation, and differentiation of hematopoietic progenitor cells. These systems can maintain the generation of clonogenic progenitors and mature granulocytes for up to 5–6 weeks because of the presence of more primitive hematopoietic cells in the in vitro culture system. These are referred to as long term bone marrow culture-initiating cells (LTBMC-IC). LTBMC systems, however, have a limited life span, and they lose the capacity to maintain LTBMC-IC in a period of 5 weeks in culture.

Human hematopoietic stem cells have been maintained for at least 8 weeks in vitro in a bone marrow stromal layer non-contact cell culture system. This system also requires additional exogenous cytokines, such as IL-3 and macrophage inflammatory protein-1α (MIP-1α), as well as diffusible marrow stromal cell factors. Of these factors, IL-3 is a multipotent stimulatory cytokine, whereas MIP-1α is presumed to act as an inhibitor of differentiation. The long term maintenance of stem cells was tested by the ability to maintain LTBMC-IC. These studies suggested that where human bone marrow stromal cells are plated, they may produce soluble factors that induce early differentiation of very primitive progenitor cells and prevent their terminal differentiation (Verfaillie, C. M., Blood 82: 2045–2053, (1993)). Up to the present time, however, it has not been possible to maintain LTBMC-IC in vitro for more than a few days with artificial mixtures of various cytokines in the absence of a marrow stromal cell layer. Accordingly, providing continuously growing stem cells is of extreme clinical importance, particularly for the ex vivo maintenance and amplification of hematopoietic stem cells for gene therapy, and for the treatment of cancer, and viral conditions such as AIDS, etc.

Immortalized bone marrow stromal cell lines have been previously produced and utilized to study the role of the microenvironment milieu they provide in the maintenance of stem cells, in the proliferation of progenitor cells, and in their differentiation. In these studies, the immortalization agent used was either the SV40 virus itself or its large T antigen gene. However, most all of the established cell lines from both human and mouse bone marrow have been fibroblast in origin. Most recently, human bone marrow stromal cell lines were immortalized with the aid of human papilloma virus E6/E7 (Roecklein, B. A., and Torok-Strob, B. (1995). Blood 85: 997–1005). One of the clones obtained was capable of maintaining colony forming cells for up to 8 weeks, a period of time similar to the LTBMC systems described above.

Human bone marrow stromal cells consist of several different cell types, including fibroblasts, adipocytes, endothelial cells, osteoblasts, and macrophages. There are also other poorly defined interstitial-like cells (stromal cell types). Only few of these cell types, however, have been immortalized and their role, thus, in the maintenance, growth, and differentiation of HSCs, remains elusive. Of these, bone marrow microvascular endothelial cells of human origin have recently been shown to support the long-term proliferation and differentiation of myeloid and megakaryocytic progenitor cells (Rafii. S., et al., Blood 86: 3353–3363 (1995)). These progenitor cells, which proliferate in the presence of bone marrow microvascular endothelial cells, however, are not capable of generating erythroid and/or lymphoid lineage cells. In addition, the total number of the thus produced total progenitor cells declined steadily, and disappeared after 7–8 weeks.

Bone marrow endothelial cells are known to produce a number of known cytokines. The present inability of maintaining continuously growing progenitor cells capable of generating erythroid cells, and the gradual decrease in their number clearly shows the inability of the prior art cells for producing stem cell/progenitor cell maintenance factors. It is desirable, therefore, to identify other stromal cell types that can maintain HSCs, are capable of producing myeloid, erythroid, and lymphoid cells in vitro for an extended period of time.

Accordingly, there is a need for the production of continuously growing hematopoietic cells, including undifferentiated stromal and hematopoietic cells, differentiated hematopoietic cells, such as megakaryocytes, dendritic cells, red blood cells (RBCs), and macrophages, suitable for use in in vitro and in vivo cell therapy. In addition, there is also a need for an in vitro system, which will permit the ex vivo expansion of totipotent hematopoietic cells, which are suitable for bone marrow transplantation, gene therapy, cell therapy, and the like.

SUMMARY OF THE INVENTION

This invention relates to transfection vectors and vector-transfected immortalized stromal cells, which remain undifferentiated in culture for prolonged periods of time. The thus obtained cell lines correspond to cell types commonly present in the bone marrow of mammals, including humans.

They may be obtained by introducing combinations of oncogenes into bone marrow mononuclear cells (MNNC) by a high efficiency peptide mediated gene transfer method. Different selective growth media may be utilized to develop different stromal cell types.

The immortalized stromal cell lines may be used to develop immortalized hematopoietic (progenitor) cell lines capable of differentiation into either myeloid or erythroid lineages. The immortalized undifferentiated hematopoietic cell lines may be obtained, for instance, from $CD34^+$ hematopoietic stem cells isolated from either human cord blood or bone employing various of the immortalized stromal lines of the invention, including human cell lines, as a feeder layer to select transfected HSCs in the presence of a certain cytokine combinations. The progenitor cell lines may be utilized for the in vitro development of other cell lines, including dendritic cells, macrophages, megakaryocytes, and red blood cells. These cells are suitable for use in basic research, for the discovery of new cytokines and drugs, such as for the treatment of AIDS and related ailments and, more generally, for drug screening. This technology is applicable to the ex vivo expansion of bone marrow cells suitable for bone marrow transplantation, to the in vitro culture of undifferentiated hematopoietic cells, such as CD34+ cells, to the in vitro production of differentiated hematopoietic cells, such as dendritic cells, macrophages, megakaryocytes, and red blood cells (RBCs). The immortalized differentiated hematopoietic cells are suitable for the in vitro toxicological and efficacy testing of drugs. The progenitor cell lines of this invention may be grown continuously in large numbers over the immortalized stromal cell lines. This in vitro system permits, for instance, the generation of large numbers of dendritic cells, which are suitable for developing monoclonal antibodies that are highly specific to these cells. These monoclonal antibodies are clinically important, for example, in the prevention of viral, e.g., HIV, transmission to T-cells, and for in vitro immunization.

This invention also permits the use of the undifferentiated progenitor cell lines, that depend upon close contact with the stromal cell layer for its maintenance and growth, as target cells in a bioassay.

DESCRIPTION OF THE PREFERRED EMBODIMENTS

This invention arose from a desire by the inventor to improve on prior art technology and overcome the limitations imposed by the unavailability of immortalized stromal and hematopoietic cell lines. Previous attempts to provide immortalized progenitor cell lines have been unsuccessful, principally because, up to the present invention, the maintenance of oncogene transfected HSCs in the presence of different cytokine combinations invariably brought about terminal differentiation and cessation of growth. The present technology is based on the development by the inventor of certain immortalized stromal and hematopoietic stem cell lines. The hematopoietic stem cell lines may remain undifferentiated or be induced to differentiate.

Hematopoietic progenitor cells are strongly associated with the adherent population of stromal cells in long term bone marrow cultures (Coulombel, L., et al, Blood 62: 291–297 (1983)), and their anchorage to stromal cell microenvironment plays an important role in initiating the colony forming potential of quiescent stem cells (Berardi, A. C., et al., Science 267: 104–108 (1995)). Based on the available information, the inventor conceived that any attempt to develop a permanent human hematopoietic progenitor cell line capable of differentiating into both myeloid and erythroid lineages must contain a stromal cell component. This could be the stromal cell itself, over which transfected stem cells may be selected to obtain a progenitor cell line.

Some of the extended life or immortalized cells provided herein are derived from stromal cells, and are capable of supporting the continuous growth of other type of hematopoietic cells of extreme therapeutic importance, such as hematopoietic CD34+ cells, derived from a variety of tissues and mammalian species. Human bone marrow and cord blood cells are examples provided in the exemplary disclosure. The hematopoietic progenitor cell lines may be maintained in vitro in their undifferentiated state, in the presence of the prolonged life stromal cell lines, generally with a combination of cytokines, such as interleukin-3 (IL-3), interleukin-6 (IL-6), GM-CSF, G-CSF, tumor necrosis factor-$\alpha$ (TNF-$\alpha$), interleukin-1 (IL-1), MIP-1$\alpha$, and stem cell factor, among others, and mixtures thereof. The stromal cells may be laid over a substrate, and the hematopoietic progenitor cells maintained in vitro over the stromal cells during incubation. When the prolonged life stem cells are grown in the presence of the stromal cell lines, but in the absence of any exogenously added cytokines, their growth rate is slower as compared with that obtained in the presence of cytokines. In addition, when the prolonged life stem cells are grown with the same combination of cytokines, but in the absence of the stromal cells, they continue undifferentiated growth for a short period of time, in some cases of about two weeks, and then they spontaneously undergo terminal differentiation, which is accompanied by a total cessation of cell growth. The presence of the prolonged life stromal cells in the cell culture, thus. not only maintains the growth of the progenitor cells, but prevents the cells from undergoing irreversible differentiation, possibly by a negative regulatory mechanism.

When the immortalized stem cells are grown in the absence of the prolonged life stromal cell lines, and in the presence of factors, such as GM-CSF, TNF-$\alpha$, and IL-4 or M-CSF, among others, they develop into myeloid, erythroid and/or megakaryocytic cells, such as dendritic cells and macrophages. Cells such as dendritic cells and macrophages are terminally differentiated cells that may be utilized as a test system for testing the effect of drugs on, for example, cell differentiation or toxicity.

The treatment of immortalized stem cell-derived cell lines with cytokines, such as GM-CSF, TNF-$\alpha$, and IL-4 or M-CSF, generates differentiated dendritic cells and macrophages, respectively. The extended life transformed stromal cell stem/cell system may also be utilized as an in vitro model for the determination of bone marrow toxicity of specific drugs. Thus, with an in vitro system, such as the one developed herein, a large number of compounds may be tested in a short period of time.

The present invention may be applied to developing cell lines, including blood monocytes and macrophages, from non-dividing cells, such as human peripheral stem cells, with a complex of a synthetic polypeptide with one or more DNA molecules, by taking advantage of the high negative charge density on the polynucleotide. To this end, D- or L-isomers of amino acids in the synthetic polypeptides, about 10 to 50 basic amino acid long, comprising a DNA-binding sequence rich in basic amino acids, such as lysine, arginine and/or ornithine. The DNA-binding sequence may be a homopolymer of a basic amino acid, or it may comprise different kinds of basic residues. The DNA binding sequences must be of adequate length to bind polypeptides and/or DNAs, yet not so long that it precipitates out of the solutions employed in the present methodology, as discussed below. The synthetic polypeptide of the present invention also generally contains an amino acid sequence corresponding to a nuclear localization signal (NLS) sequence. A representative sample from the diverse range of nuclear localization signals which have been identified are listed in Table I below.

an NLS peptide, which is typically about 6 to 15 amino acids long, facilitates the transport of the associated DNA into the nucleus. This method has a highly efficient, stable and transient gene expression, principally because the synthetic polypeptide promotes the transport of the transfected gene into the nucleus of the host cell. Once inside the nucleus, the introduced DNA is immediately available to the transcription machinery, and may be expressed transiently.

TABLE 1

| Source | Nuclear Protein | Deduced Signal Sequence |
| --- | --- | --- |
| Yeast | MATα2 | K—I—P—I—K (SEQ. ID NO: 1) |
|  |  | V—R—I—L—E—S—W—F—A—K—N—I (SEQ. ID NO: 2) |
| SV40 | Large T | P—K—K—K—R—K—V (SEQ. ID NO: 3) |
| Influenza virus | Nucleoprotein | A—A—F—E—D—L—R—V—R—S (SEQ. ID NO: 4) |
| Yeast | Ribosomal protein L3 | P—R—K—R (SEQ. ID NO: 5) |
| Polyoma virus | Large T | V—S—R—K—R—P—R—P—A (SEQ. ID NO: 6) |
| SV40 | VP1 | A—P—T—K—R—K (SEQ. ID NO: 7) |
| Adenovirus | E1a | K—R—P—R—P (SEQ. ID NO: 8) |
| SV40 | VP2 (VP3) | P—N—K—K—K—R—K (SEQ. ID NO: 9) |
| Frog | Nucleoplasmin | R—P—A—A—T—K—K—A—G—Q—A—K—K—K—K—L—D (SEQ. ID NO: 10) |
| Rat | Glucocorticoid receptor | K—K—K—I—K (SEQ. ID NO: 11) |
| Monkey | v-sis (PDGF B) | R—V—T—I—R—T—V—R—V—R—R—P—P—K—G—K—H—R—K (SEQ. ID NO: 12) |
| Yeast | Histone 2B | G—K—K—R—S—K—A (SEQ. ID NO: 13) |
| Chicken | v-rel | K—A—K—R—S—K—A (SEQ. ID NO: 14) |
| Influenza | NS1 | D—R—L—R—R (SEQ. ID NO: 15) |
|  |  | P—K—Q—K—R—K (SEQ. ID NO: 16) |
| Frog | N1 | V—R—K—K—R—K—T (SEQ. ID NO: 17) |
|  |  | A—K—K—S—K—Q—E (SEQ. ID NO: 18) |
| Human | c-myc | P—A—A—K—R—V—K—L—D (SEQ. ID NO: 19) |
|  |  | R—Q—R—R—N—E—L—K-4-S—F (SEQ. ID NO: 20) |
| Human | lamin A | T—K—K—R—K—L—E (SEQ. ID NO: 21) |
| HTLV-1 | Rex (p27$^{III}$) | P—K—T—R—R—R—P (SEQ. ID NO: 22) |
|  |  | S—Q—R—K—R—P—P (SEQ. ID NO: 23) |
| Adenovirus | $_p$TP | R—L—P—V—R—R—R—R—R—R—V—P (SEQ. ID NO: 24) |
| HIV-1 | Tal | G—R—K—K—R (SEQ. ID NO: 25) |
| Frog | Lamin L$_1$ | V—R—T—T—K—G—K—R—K—R—I—D—V (SEQ. ID NO: 26) |
| Rabbit | Progesterone receptor | R—K—F—K—K (SEQ. ID NO: 27) |
| HIV-1 | Rev | R—R—N—R—R—R—R—W (SEQ. ID NO: 28) |
| Human | PDGF A-chain | P—R-3-S—G—K—K—R—K—R—K—R—L—K—P—T (SEQ. ID NO: 29) |
| Mouse | c-abl | K—K—K—K—K (SEQ. ID NO: 30) |
| Adenovirus | DBP | P—P—K—K—R (SEQ. ID NO: 31) |
|  |  | P—K—K—K—K (SEQ. ID NO: 32) |
| Chicken | c-erb-A | S—K—R—V—A—K—R—K—L (SEQ. ID NO: 33) |
| Human | c-myb | P—L—L—K—K—I—I—Q (SEQ. ID NO: 34) |
| Human | N-myc | P—P—Q—K—K—I—K—S (SEQ. ID NO: 35) |
| Human | p53 | P—Q—P—K—K—K—P (SEQ. ID NO: 36) |
| Human | Hsp 70 | F—K—R—K—H—K—K—D—I—S—Q—N—K—R—A—V—R—R (SEQ. ID NO: 37) |
| Hepatitus B virus | Core protein | S—K—C—L—G—W—L—W—G (SEQ. ID NO: 38) |
| Chicken | Eis1 | G—K—R—K—N—K—P—K (SEQ. ID NO: 39) |
| Yeast | Ribosomal protein L29 | K—T—R—K—H—R—G (SEQ. ID NO: 40) |
|  |  | K—H—R—K—H—P—G (SEQ. ID NO: 41) |
| Protein |  | Nuclear Localization Signals |
| TGA-1A (tobacco) |  | R—R—L—A—Q—N—R—E—A—A—R—K—S—R—L—R—K—K (SEQ. ID NO: 42) |
| TGA-1B (tobacco) |  | K—K—R—A—R—L—V—R—N—R—E—S—A—Q—L—S (SEQ. ID NO: 43) |
|  |  | R—Q—R—K—K (SEQ. ID NO: 44) |
| O2 NLS B (maize) |  | R—K—R—K—E—S—N—R—E—S—A—R—R—S—R—Y—R—K (SEQ. ID NO: 45) |
| Nla (Polyvirus) |  | K—K—N—Q—K—H—K—L—K—M-32aa-K—R—K (SEQ. ID NO: 46) |
| VirD2 (Agrobacterium) |  | K—R—P—R—E—D—D—D—G—E—P—S—E—R—K—R—E—R (SEQ. ID NO: 47) |
| VirE2 NSE1 (Agrobacterium) |  | K—L—R—P—E—D—R—Y—I—Q—T—E—K—Y—G—R—R (SEQ. ID NO: 48) |
| VirE2 NSE2 (Agrobacterium) |  | K—T—K—Y—G—S—D—T—E—I—K—L—L—S—K (SEQ. ID NO: 49) |
| O2 NLS A (maize) |  | M—E—E—A—V—T—M—A—P—A—A—V—S—S—A—V—V—G—D—P (SEQ. ID NO: 50) |
|  |  | M-3-Y—N—A—I—L—R—R—K—L—E—E—D—L—E (SEQ. ID NO: 51) |
| R NLS A (maize) |  | G—D—R—R—A—A—P—A—R—P (SEQ. ID NO: 52) |
| R NLS M (maize) |  | M—S—E—R—K—R—R—E—K—L (SEQ. ID NO: 53) |
| RNLS C (maize) |  | M—I—S—E—A—L—R—K—A—I—G—K—R (SEQ. ID NO: 54) |

(See, Garcia-Bustos et al., Biochem. Biophys. Acta 1071: 83 (1991); Raikhel, N., Plant Physiol. 100: 1627 (1992), and Citovsky, V. et al., Science 256: 802 (1992)). The contents of each of these publications relevant to this technology are hereby incorporated by reference. In the present invention, Simultaneously, the introduced DNAs are also in the process of getting integrated into the host chromosome to give rise to stable expression. Thus, the method of the instant invention achieves both transient and stable expression of introduced DNA. Transient gene expression results when the method of gene transfer results in the introduction of the DNA sequences into the nucleus in an non-integrated form. Transient transfection is measured 24 to 72 hours after transfection by assays that measure gene expression of the transfected gene(s). In contrast, stable expression of the encoded protein results when the transferred DNA sequences are stably integrated into the chromosomal DNA of the target cell. Stable transfectants remain capable of expressing a transfected DNA after two weeks or longer when a marker or exogenous gene is additionally incorporated. Commonly used assays monitor enzyme activities of chloramphenicol acetyltransferase (CAT), LAC-Z, β-galactosidase (β-Gal), β-glucuronidase (β-Gls), luciferase, or human growth hormone, each of which may be contained in the present invention.

The NLS domain of the synthetic peptide is defined herein based on known endogenous peptide sequences identified as follows.

(1) Sufficient to redirect a cytoplasmic protein to the nucleus.

(2) Necessary for directing a nuclear protein to the nucleus.

Methods for assessing an NLS peptide's ability to direct protein to the nucleus are known in the art. (See, Garcia-Bustos, et al., supra; Sandler at al., S. Cell Biol. 109: 2665 (1989); Citovsky et al., supra). The pertinent contents of the cited publications are hereby incorporated by reference. For example, an NLS peptide or a natural protein containing an NLS may be fused to an otherwise non-nuclear protein, by either synthetic or recombinant production. The hybrid protein may be assessed for its ability to target the non-nuclear protein to the nucleus. The presence of the non-nuclear protein in the nucleus may be determined, e.g., by a functional assay or immunofluorescence. An illustrative assay entails the histochemical determination of a product produced by the non-nuclear protein, such as a colorimetric marker produced by β-gal or GUS. A colorimetric marker includes an enzyme that can catalyze a reaction with a substrate to elicit a colored product which can be detected or measured by a variety of means, such as standard fluorescence microscopy, flow cytometry, spectrophotometry or colorimetry. Immunofluorescence relates to detecting the presence of the non-nuclear protein in the nucleus by means of an antibody specific for the targeted protein. In the past, NLS peptides have been studied to assess their ability to target reporter proteins to the nucleus. There has been no suggestion heretofore, however, for using an NLS peptide to target a polynucleotide to the nucleus of a eukaryotic cell. A preferred NLS domain contains a short stretch of basic amino acids like the NLS of the SV40 virus large T antigen (PKKKRKV) (SEQ. ID NO: 3), which is an NLS that has been shown to be effective in mammalian cells (basic residues are highlighted). Another preferred NLS domain consists essentially of short hydrophobic regions that contain one or more basic amino acids (KIPIK) (SEQ. ID NO: 1), which is like the NLS of mating type a2. The NLSs that transport DNA into the plant cell nucleus are often bipartite, which means that they are usually comprised of a combination of two regions of basic amino acids separated by a spacer of more than four residues (see stippled segments in Table I above), such as the Xenopus nucleoplasmin (KRPAATKKAGQAKKKK) (SEQ. ID NO: 55). The NLS peptide of the present invention may, thus, be designed to accommodate different host cells, such as mammalian mononuclear and stem cell hosts.

One synthetic polypeptide suitable for use with the present invention, thus, comprises a DNA binding domain, and an NLS peptide domain, which are separated by a third element, a hinge region of neutral amino acid, to minimize steric interference between the two domains. For this purpose, the hinge region may be about 6 to 25 amino acids long, and may contain a stretch of small neutral amino acids, preferably without bulky hydrophobic or ionic side chains. The NLS sequence maybe located at either the amino-terminus or the carboxy-terminus of the synthetic peptide. The two domains, i.e., the basic amino acid sequence and the NLS sequence may be interchanged without affecting the high gene transfer efficiency. As indicated previously, such a synthetic polypeptide generally binds electrostatically to the DNAs that are to be introduced into the target cell. The weight ratio of polypeptide to DNAs in the resulting complex is generally about 1:1 to 1:10; for example, 1 pg polypeptide to 1 to 10 pg of polynucleotide. However, other ratios are also contemplated herein. In accordance with the present invention, the entry of the DNA-polypeptide complex into cells may be promoted by treating target cells with a hypertonic solution, followed by hypotonic treatment of cells in the presence of the gene-peptide complex. (See, for example, Okada and Rechsteiner, Cell 29: 33 (1982)). A suitable hypertonic solution may contain both polyethylene glycol (PEG) and sucrose, preferably at a concentration of about 0.3 to 0.6M and about 10 to 25%, respectively, and is hereinafter referred to as "primer". (Okada et al., supra; T. Takai et al., Biochem. Biophys. Acta 1048: 105 (1990)).

The methodology of the present invention has been used to develop stable transfectants of different cells, to thereby obtain cell lines that retain many of the characteristics of the cognate primary cells. Cell lines developed from primary cells in accordance with the present invention are herein called "extended life" or "immortalized" cell lines. The thus developed cell lines are stable transfectants, which retain almost all the characteristics of the cognate primary cells, even in their late passages. The types of cells that may be converted to immortalized cell lines. according to the present invention, depend solely on the availability of primary target cells and/or the ability to isolate the primary cells from the desired source. In this regard, the inventive methodology is not limited to cell types amenable to transformation. In addition to the cell types already mentioned, the present invention may be applied generally to primary mammalian cells, including pancreatic beta cells, liver and kidney cells, and other hematopoietic stem cells, of human and other animal origin, among others.

Although the methods of the present invention have been developed to produce immortalized cell lines from human mononuclear and stem cells, which are normally non-dividing, but is also applicable to other types of cells originating from all mammalian species. The present invention finds application as well in both ex vivo and in vivo gene therapies, where genetic material is transferred into specific cells of a mammal. Ex vivo gene therapy entails the removal of target cells from the body, transduction of the cells in vitro, and subsequent reintroduction of the modified cells into the patient.

A gene therapy pursuant to the present invention generally involves the ex vivo introduction into a cell type obtained from the mammal of polynucleotides or genes that cause the production of cytokines or other missing gene products, and the subsequent transfer of the in vivo gene transferred cells into the same or a different mammal. The method of the present invention is advantageous in that it may be used in gene therapy requiring either stable or transient gene expression. Transient expression of a gene is preferred when expression of an exogenous product is needed only for a short period of time, and a rapid clearance of the gene product and its vector is desirable. Transient expression is also desirable when the prolonged effects of the protein's expression are unknown. Stable expression in gene therapy is needed when the patient has a genetic defect that is incompatible with life. Such genetic defects include but are not limited to the lack of production of needed gene products. (Mulligan, Science 260: 926 (1993)). A gene therapy, e. g., involving the ex vivo manipulation of cell obtained from the same or another mammal with matched immuno-compatibility markers, e. g., HLA type markers, pursuant to the present invention, may also involve the in vitro introduction of DNA into stem cells, and the subsequent transplantation into the mammal's body. The stable transfer of genes (polynucleotides) into a target tissue using this method may be conducted with a ligand selectively binding the target receptor conjugated to the synthetic polypeptide. The polypeptide-ligand combination may be complexed, and then introduced into the host organism through the blood circulation. When this complex reaches a target tissue, it is taken up by cells containing the target receptor for the ligand through a receptor-mediated process. The NLS portion of the polypeptide-ligand coinplexqthe complex ensures that the vector enters the nucleus, stably integrates the introduced gene into the host chromosome and, thereby, corrects the genetic defect in the host. Cell-specific receptors are well known to those of skill in the art, as are receptor and target-specific ligands, which may be used in vector complexes for receptor-mediated gene transfer. (Michael, S. I., et al., J. Biol. Chem. 268: 6866 (1993)). When the liver is the tissue targeted for gene therapy, the DNAs may be complexed to a synthetic glycoprotein that targets the complex to a receptor on these cells. For example, a cell type-specific receptor, such as an asialoglycoprotein, may be chemically linked to the carboxy terminus of the synthetic polypeptide molecule of the transfection vector, to deliver the foreign gene directly into liver cells. An additional hinge region may be incorporated into the molecule before chemically linking the polypeptide molecule to a cell type-specific ligand molecule, such as an asialoglycoprotein or a cell-specific monoclonal antibody. The present method greatly improves on the art of cell-specific targeting of receptor-mediated transfection by providing stable expression by increasing the stable integration of foreign DNAs in a host cell using the synthetic polypeptide molecules of the present invention.

A variation of the receptor-mediated gene transfer method employs the coupling a synthetic polypeptide as described above to monoclonal antibodies which recognize a cell surface antigen on target cells. (Naruyama et al., P.N.A.S. (USA) 87: 5744 (1990)). The thus coupled monoclonal antibody and synthetic polypeptide are then complexed with a DNA encoding the required or desired protein. This complex will target the DNA to the cells expressing the corresponding cell surface antigen. Other tissues of the human body may also be targeted for gene therapy in accordance with the present invention using the disclosed methods. Any mammalian target tissue is suitable in this context as long as it is susceptible to genetic modification according to the present invention.

The present invention is further described with reference to the following examples, which are only illustrative, not limiting, of the invention.

EXAMPLES

Development of Immortalized Human Stromal Cell Lines

Standard institutional procedures were strictly adhered to in all experimental work performed, and informed consent from volunteer donors was obtained.

Example 1

Preparation of Bone Marrow Mononuclear Cells

Bone marrow (BM) aspirates are collected with heparin, diluted 1:1 with DMEM/F12 (50/50) medium containing 2% heat inactivated fetal bovine serum, layered over an equal volume of Ficoll-hypaque (Histopaque, Sigma Chemical Company), and centrifuged to isolate mononuclear cells. The BM mononuclear cells are then used for transfections with varying combination of oncogenes under different growth conditions that are suitable for selecting each of the bone marrow stromal cell types.

Example 2

Gene Transfer Procedure

The gene transfer method utilized involves the use of a synthetic peptide 25 amino acids long as a carrier of DNA into cells and into the nucleus. The synthetic peptide consists of three domains a nuclear localization signal (NLS) at the N-terminal end, a hinge region in the middle, and a basic amino acid region consisting of a stretch of lysine residues at the C-terminus.

Example 3

Production of A Synthetic Polypeptide Molecule

An example of a synthetic polypeptide molecule of the present invention is one consisting of the amino acid sequence PKKKRKVSGGGGGKKKKKKKKKKKK (SEQ. ID NO: 56). Such a peptide can be synthesized, using standard methods of peptide production, and purified by standard methods using high pressure liquid chromatography (HPLC).

Example 4

Preparation of DNA-polypeptide Complex

The DNA to be introduced into cells is complexed with the synthetic peptide at a suitable molar ratio in a hypotonic medium, and the DNA-peptide complex is added to cells that have been treated in a hypertonic medium. This treatment results in quick delivery of the DNA-peptide complex into the nucleus because of the NLS in the complex.

The DNA or other polynucleotide to be transfected, such as a plasmid containing a gene for a drug resistance marker or coding a protein needed for expression in the host cell, is complexed to a synthetic polypeptide molecule in different weight ratios in an isotonic buffer solution. For example, the weight ratio of DNA: polypeptide may be about 1:1 to 10:1, although ratios outside of this range may be evaluated empirically for achieving the objects of the present invention. An isotonic buffer solution such as Hanks buffered salt solution or HEPES buffered saline may be used for complexing the DNA to the polypeptide.

After the DNA-polypeptide complex is formed, it is made hypotonic. The complex solution is hypotonic when it has a lesser osmotic pressure than about 0.15M or 0.9% solution of NaCl. For example, the complex in isotonic buffer may be made 40–55% hypotonic or 0.075M simply by adding an amount of distilled water about equal to the volume of the complex in isotonic buffer.

Example 5

Preparation of Cells & Transfection Procedure

While the DNA-polypeptide complex is formed, the cells to be transfected either remain attached to a substratum, such as a tissue culture dish, or are pelleted (for cells that grow in suspension). The gene transfer method of the present invention was used to generate extended life cell lines from different human primary cells. Most of the primary cells have a limited in vitro life span. The following cell types were employed to test the efficacy of the inventive method to generate extended-life cell lines by transfer of various oncogenes, either singly, in pairs of combinations, or combinations of more than two oncogenes. (Rhim, J. S. et al., Oncogene 4:1403 (1989)).

Example 6
Production of Immortalized Cell Lines

The host cells are primary cells isolated from different species, human or other mammalian species, which have only a limited in vitro life span. The isolation of primary cells from various tissue sources are well known to those of skill in the art. In order to extend their life, primary cells may be transfected with different oncogenes, such as SV40 large T-antigen, polyoma large T-antigen. adenovirus E1A and E1B, v-fms, Bc12, myc and ras, among others. These oncogenes can be used either alone, in pairs of various combinations, or in combinations of more than two oncogenies. In addition to oncogenes, other genes or fragments thereof may also be used. For example, genes that are important for DNA synthesis and normally active during the S phase of the cell cycle, such as the dihydrofolate reductase gene (DHFR), thymidine kinase gene, thymidylate synthetase gene, a DRTF1/E2F transcription factor encoding DNA, or DNA encoding the E2F transcription factor may be complexed to a synthetic polypeptide and used to extend the life of primary cells. The human DHFR gene complexed to synthetic polypeptide may be introduced into primary cells to produce extended life cell lines. DNAs encoding a transcription factor that is active during the S phase of the cell cycle are particularly useful in the method of the instant invention. (La Thangue, N. B., Trends in Biochem. Sci. 19: 108 (1994); Johnson, D. C., et al., Nature 365: 349 (1993), the respective contents of which are hereby incorporated by reference).

Example 7
Transfection of MNNC Cells

MNNC were transfected with different combinations of oncogenes. The SV 40 large T-antigen gene, the transcription factor E2F gene, and the adenoviruses E1A and E1B, were effective in giving rise to immortalized stromal cell lines.

The cells were treated with a hypertonic primer solution, such as a concentration of about 0.3M–0.6M sucrose and 10% PEG in either Tris-HCl or HEPES (pH=7.2) buffered solution, for 3–5 min. at room temperature. The primer solution was then removed.

The hypotonic complex solution was then added to the cells that had been treated with the primer solution, and the cells remained in the hypotonlic DNA-polypeptide solution for about 3–4 minutes. Fresh medium was then added to the cells to rinse away any excess of the DNA-polypeptide solution. Thereafter, the cells were grown normally.

Because untreated primary cells only have a limited life span in vitro, their ability to grow continuously in culture after receiving the treatment of the present invention serves to select for extended life cell lines. No other drug selection markers need to be used to select for extended life cell lines derived from primary cells. The treated cells were plated in their appropriate growth media and passed after the cells reached confluency. A parallel set of a control untreated primary cells were cultured under the same growth conditions. Typically, control primary cells stop growing after about 4–10 passages, depending upon the cell type (cell split ratio was usually 1:4 by surface area). In contrast, continuously growing cell lines were obtained from different primary cell types described in the following examples.

Example 8
Isolation of Immortalized Lines from Different Stromal Cell Types

Four different growth media were used to isolate four different cell types.

(a) Immortalized EG Cells

Human bone marrow mononuclear (HBMM) cells were transfected with one combination of oncogenes. adenoviruses E1A and E1B, and then selected in endothelial cell growth medium, containing EGF, bovine pituitary extract, heparin, and hydrocortisone (EG Medium) obtained from Clonetics Corporation, CA. This procedure gave rise to a continuously growing population of cells that were spindle shaped. These cells resembled bone marrow endothelial cells (BMEC) that have been described recently by Rafii et al. (Rafii, S., et al., Blood 84: 10–19(1994)). The transfected cell population has been grown for several passages, and is still continuously growing, whereas mock transfected or cells transfected with other combination of oncogenes ( SV40 large T and E1A virus genes) did not grow very well beyond passage four. The immortalized cells produced herein were characterized for the expression of endothelial cell specific markers, such as IL-1 inducible expression of ELAM-1 and VCAM-1, both basal and IL-1 inducible expression of ICAM-1, and factor VIII. These results clearly indicate that these cells express functions that are characteristic of other endothelial cells.(b)

(b) Immortalized IF, D & SK Stromal Cell Lines

Transfected human bone marrow cells were also selected in the following three different media.

(1) IMDM supplemented with 12.5% horse serum 12.5% fetal bovine serum, hydrocortisone, and mercaptoethanol (IFHCM medium).

(2) 50/50 DMEM/F12 ( Mediatech) supplemented with 10% fetal bovine serum (DF10 medium).

(3) MCDB 120 (Clonetics Corporation) supplemented with EGF, insulin, fetuin, and 5% fetal bovine serum (SK medium).

The cells growing in the last 3 different media were morphologically distinct cell types. The 4 types of cells have now been grown in the above 4 media for several passages, and they behave like, and are likely to be, immortalized cell lines. The cells selected in IFHCM medium grew as adipocytes, and contained a lot of fat droplets. Another characteristic feature of these cells was copious secretion of extra cellular matrix (ECM).

The above described 4 different stromal cell types selected in EGM, IFHCM, DF10, and SK are referred to as EG, IF, D, and SK cell types respectively. These bone marrow stromal cell lines have distinct morphological phenotypes, and require different growth factors for their continuous growth. They were used in different combinations to create an in vitro system providing critical conditions for ex vivo maintenance and amplification of pluripotent hematopoietic cell lines suitable for bone marrow transplantation and other gene therapy applications.

Development of In Vitro System including Stromal Cells (SC) & SC-contact-dependent Hematopoietic Progenitor Cell Lines

Example 9
Layering over SC & Transfection of MNNCs

The stromal cell lines EG and SK, described in Example 8 above, were used as feeder layers for selection of transfected HSCs. CD34$^+$ HSCs were isolated from cord blood and bone marrow MNNC using a commercially available panning device (Applied Immune Sciences Corporation.

CA). The cells were then transfected with two different combinations of oncogenes, SV40 large T-antigen and E2F1 transcriptional factor gene, and the adenovirus E1A and E1B genes, respectively. The transcriptional factor gene has been shown to induce DNA synthesis in cells arrested at the S phase of the cell cycle (Johnson, D. G., et al, Nature 365: 349–352 (1993)), and has also been shown to immortalize some cell types (Singh, P., et al., EMBO Journal 13: 3329–3338 (1994)). Transfection of various primary human cell types, such as different endothelial cells, have shown that the E2F1 gene alone was not capable of immortalizing human cell types, but that two genes are necessary to completely immortalize cells. After the $CD34^+$ HSCs were transfected with the combination of genes mentioned earlier, they were separately plated over stromal cell types EG and SK in their respective media. The feeder layers EG and SK were treated with mitomycin C (5 μg/ml for 1 hour at 37° C.), and extensivly washed prior to layering the HSCs on them.

Example 10
Selection of Transformants

When the transfected cells were selected in either media without any additional cytokines, the transfected cells grew for about 4 weeks, and eventually stopped growing. The transfected cells were also selected over the stromal cell layer in their respective medium supplemented with 5 ng/ml IL-3 alone, or with 5 ng/ml each of IL-3 and stem cell factor (SCF, c-kit ligand).

The HSCs selected in both media gave rise to a floating population of cells. These cells have now been grown for several passages over mitomycin treated stromal feeder layers in continuous culture, and are referred to as progenitor cell lines. These cells are undifferentiated and have maintained a smooth spherical shape. Progenitor cell lines selected over both stromal cell types with IL-3 alone, or with IL-3 plus SCF (3S medium) were used for further analysis.

Transfected HSCs selected in 3S medium, but without the corresponding feeder layer, grew very poorly for a couple of weeks and eventually stopped growing because of the occurrence of terminal differentiation. This clearly indicates that the feeder stromal cell layer is critical for the growth of immortalized HSCs as well as for preventing HSCs from undergoing terminal differentiation.

Example 11
In Vitro Development of Differentiated Cells obtained from Immortalized Undifferentiated Progenitor Cell Lines The progenitor cell lines selected with IL-3 alone, and with the 3S medium (IL-3 plus SCF), respectively, were tested for their ability to undergo differentiation into different lineages. Floating population of cells were removed from the stromal cell layer by gentle trituration, and they were then extensively rinsed and plated in IMDM supplemented with 10% fetal bovine serum with the following additional cytokine supplementation.

a. 2 ng/ml each of GM-CSF and TNF-α to test for the ability to develop into dendritic cells (Caux, C., et al., Nature 360: 258–261 (1992); Caux, C., et al., J. Exp. Med. 180: 1263–1272 (1984));

b. 5 ng/ml of M-CSF to test for ability to differentiate into macrophages.

The progenitor cell lines selected in both media were capable of generating differentiated cells, including dendritic cells and macrophages, when cultured with appropriate cytokines in the absence of the stromal cell layer.

Example 12
Selection & Characterization of Dendritic Cells obtained from Immortalized Undifferentiated Progenitor Cell Lines The progenitor cell lines were treated as described in Example 11 above. The cells were then plated with 2 ng/ml each of GM-CSF and TNF-α for 6–8 days, during which time they differentiated into dendritic cells. However, other concentrations of these factors and other factors may also be utilized.

The dendritic cells were then characterized for the expression of various immunological cell markers as follows. The cell line was attached to a polylysine coated plate, fixed, and treated with surface marker specific antibodies. The cells were then treated with biotin-conjugated anti-mouse IgG, followed by treatment with streptavidin conjugated-galactosidase. X-gal substrate was used for color development. These cells were strongly positive for all three HLA class II molecules, and negative for monocyte, and T- and B-cell specific markers. The results are shown in Table II below.

TABLE II

Expression of Various Surface Markers on Dendritic Cells Generated In Vitro

| Marker | Expression |
| --- | --- |
| CD3 | − |
| CD14 | − |
| CD20 | − |
| CD22 | −/+ |
| CD40 | ++ |
| CD45 | ++ |
| HLA-DP, DQ, DR | ++++ |

− No reaction
+ to ++++ Intensity of reaction

Example 13
Selection of Macrophages from Immortalized Undifferentiated Progenitor Cell Lines The progenitor cell lines were treated as described in Example 11 above. Then, the cells were plated with 10 ng/ml M-CSF for 6–8 days when they developed into macrophages. However, other amounts of M-CSF and other factors may also be utilized. They were additionally tested for a phagocytosis, macrophage phenotype, using fluorescent beads (Sigma Chemical Company). These cells were found to be highly phagocytic. Other macrophage specific markers, such as lysozyme, nonspecific esterase, peroxidase, and LPS stimulated IL-1 expression were also tested using published methods (Schwarzbaum, S., et al., J. Immunol. 132: 1158–1162 (1984)).

Example 14
Method of Screening Anti-Viral Drugs

These results indicate that it is now possible to obtain differentiated dendritic cells at will using the progenitor hematopoietic non-differentiated cell lines described in this application. The differentiated cell lines are used to address some very important unresolved questions regarding their role in the development of AIDS.

The results from these studies lead to new treatments for viral infections afflicting lymphocytes, including AIDS. The present immortalized dendritic and other cell lines may be stably infected with viruses, including HIV, and he thus infected cells used to screen drugs that, for example, abrogate viral replication, e. g., HIV replication, in these cell types. Either the undifferentiated progenitor cell lines or the in vitro generated dendritic cells and macrophages therefrom may be stabile infected with a virus, such as HIV, by known methods.

These HIV-infected cells are then utilized to screen drugs that prevent the replication and/or maintenance of the virus, e. g., HIV, within the cells, the transmission of the virus to other cells, e. g., helper T-cells, or the formation of other forms, e. g., synctia by an HIV-transfected cell/T-cell mixture, utilizing technology and bioassays known in the art.

In addition, dendritic cell lines pulsed with virus, e. g., HIV-1, may be used to screen drugs that prevent viral transmission, including HIV virus, to $CD4^+$ T-cells that conjugate with dendritic cells. This results in the development of new treatments for virus-associated diseases, such as HIV-related diseases and AIDS. (Cameron, P. V. et al., Science. 257: 333–382 (1992); Pope, M. et al., Cell, 78: 389–398 (1994)).

Example 15
Selection of other Cell Types from Immortalized Undifferentiated Progenitor Cell Lines The immortalized progenitor cell lines are also tested as to their development into other differentiated cell types, including neutrophils, megakaryocytes, and mast cells, by growing them with appropriate cytokines by methods known in the art (Berliner, N., et al., Blood 85: 799–803 (1995); Bartley, T. D., et al., Cell 77: 1117–1124 (1994); deSauvage, F. J., et al., Nature 369: 533–538 (1994); Lok, S., et al., Nature 369: 565–568 (1994); Rennick, D, et al., Blood 85: 57–65) (1995)). These cells, being capable of differentiating into different myeloid cells, are thus classified as hematopoietic progenitor cells.

The immortalized bone marrow stromal-progenitor cell system is, thus, capable of generating in vitro several types of differentiated hematomyeloid cells in large quantities. The ability to develop different myeloid cell types, such as dendritic cells, in vitro, in large quantities can overcome the difficulties associated with the need for continuous and repeated isolation of primary dendritic cells.

Example 16
Preparation of Polyclonal & Monoclonal Antibodies Selectively Binding to Dendritic Cells and Macrophages Polyclonal and monoclonal antibodies against myeloid cells, including dendritic cells, macrophages, megakaryocytes, platelets, and eosinophils, among others, are prepared by using standard technology. Briefly, 8 week old, female BALB/c mice, are injected with about $3\times10^6$ dendritic cells, macrophages, or other cell types generated from the immortalized progenitor cell lines. This procedure is repeated 4 times, each 10 days apart from the previous injection. Polyclonal antibodies are obtained from the serum by methods known in the art. For the preparation of monoclonal antibodies, the last injection of cells is given to the mice about 3–4 days before fusion. The spleens of the thus immunized mice are removed, and fused with, for example, SP2/O fusion partners, using known and standard prior art methods to generate hybridomas. The sera's and the hybridomas' supernatants are screened for the secretion of cell type-specific antibodies by binding to the desired cell type, permitting for the reaction of the antibody and its antigen, and then incubation with, e. g., goat anti-mouse L chain antibody. The cells are then rinsed thoroughly, and treated with $^{125}$I-streptavidin, washed extensively, and counted. Hybridomas are then selected by their ability to secrete antibodies, which react selectively and specifically with the cell type present in the immunizing injections, but not with other cell types generated in vitro from the progenitor cell lines (Graber, N., et al., J. Immunol 145: 819–830 (1990)).

These antibodies are highly specific for dendritic cells and are clinically very important, for example, to prevent the transmission of HIV to T-cells. Human polyclonal and monoclonal antibodies prepared against these cells are useful are for clinical applications.

Example 17
Stromal Cell Line/Progenitor Hematopoietic Cell Line System for Toxicity Assay The in vitro reconstituted bone marrow stromal microenvironment system in combination with the progenitor cell lines that can be grown only in contact with the stromal cell lines is useful as a system to study human bone marrow toxicity during drug development. A number of different approaches are used to test compounds for bone marrow toxicity using the stromal cell line/progenitor cell line system of the invention. Different concentrations of each test compound are added to the cell medium of different cell system incubation plates. The different doses tested reflect a broad range of physiological concentrations, and the compounds are allowed to be in contact with the cell system either for a set period of time, or the time of exposure is varied for the same concentration. The rate of cell growth, its chromosomal integrity, its ability for forming colonies in accordance with a standard soft agar colony assay, and other cellular characteristics, are tested by methods known in the art (Puelo, D. A., J. Applied Biomaterials 6:109–116 (1995); Gandhi, G., et al., Mut. Res. 346: 203–206 (1995); Bhalla, K., et al., Blood 74: 1923–1928 (1989); Mackay, J. M., et al., Carcinogenesis 16: 1127–1133 (1995); Chan, T. C. K., et al., Eur. J. Hematol. 49: 71–76 (1992)).

What is claimed as novel and unobvious In Letters Patent of the United States is:

1. A transfection vector in the form of a complex, comprising
   a polypeptide comprising a basic peptide segment, a nuclear localization segment (NLS) peptide, and a neutral hinge peptide linking the basic peptide and the NLS; and
   at least one DNA segment selected from the group consisting of oncogenes, genes associated with cell cycle regulation, and segments thereof.

2. The vector of claim 1, comprising two oncogene segments.

3. The vector of claim 1, wherein the DNA segment is selected from the group consisting of SV40 large T-antigen gene, transcriptional factor E2F gene, adenovirus E1A gene, adenovirus E1B gene, polyoma large T and small t antigen genes, dihydrofolate reductase gene (DHFR), myc, ras, papilloma virus E6/E7 genes, and fragments, mixtures, and combinations thereof.

4. The vector of claim 1, wherein the polypeptide and the DNA segment are non-covalently linked.

5. The vector of claim 1, wherein the polypeptide comprises the amino acid sequence PKKKRKVSGGGGGKKKKKKKKKKKK (SEQ.ID NO: 56).

6. The vector of claim 1, further comprising a selectively targeted ligand, which is coupled to the polypeptide.

7. The vector of claim 6, further comprising an additional hinge peptide linking the targeted peptide ligand to the polypeptide.

8. The vector of claim 6, wherein the target polypeptide comprises an antibody, a fragment thereof, or an asialoglycoprotein.

9. An immortalized stromal cell, produced by transfection of a mononuclear hematopoietic cell with the vector of claim 1.

10. The stromal cell of claim 9, being a bone-marrow or cord cell.

11. The stromal cell of claim 9, being a human cell.

12. The stromal cell of claim 9, wherein the transfected mononuclear hematopoietic cell gives rise to a continuously growing population of cells selected from the group consisting of fibroblasts, adipocytes, endothelial cells, osteoblasts, and macrophages.

* * * * *

SEQUENCE LISTING ( 1 ) GENERAL INFORMATION:

( i i i ) NUMBER OF SEQUENCES: 56

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:1:

```
Lys   Ile   Pro   Ile   Lys
1                       5
```

( 2 ) INFORMATION FOR SEQ ID NO:2:

( i ) SEQUENCE CHARACTERISTICS:
        ( A ) LENGTH:12 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:2:

```
Val   Arg   Ile   Leu   Glu   Ser   Trp   Phe   Ala   Lys   Asn   Ile
1                       5                             10
```

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:3:

```
Pro   Lys   Lys   Lys   Arg   Lys   Val
1                       5
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:4:

```
Ala   Ala   Phe   Glu   Asp   Leu   Arg   Val   Arg   Ser
1                       5                             10
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:5:

```
Pro   Arg   Lys   Arg
1
```

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:6:

```
Val   Ser   Arg   Lys   Arg   Pro   Arg   Pro   Ala
1                       5
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: Not Relevant ( D ) TOPOLOGY: Not Relevant ( x i ) SEQUENCE DESCRIPTION: SEQ ID NO:7:

Ala Pro Thr Lys Arg Lys
1               5

( 2 ) INFORMATION FOR SEQ ID NO:8:

( i ) SEQUENCE CHARACTERISTICS:
        ( A ) LENGTH: 5 amino aicds
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:8:

Lys Arg Pro Arg Pro
1               5

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:9:

Pro Met Lys Lys Lys Arg Lys
1               5

( 2 ) INFORMATION FOR SEQ ID NO:10:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:10:

Arg Pro Ala Ala Thr Lys Lys Ala Gly Gln Ala Lys
1               5                       10
Lys Lys Lys Leu Asp
        15

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:11:

Lys Lys Lys Ile Lys
1               5

( 2 ) INFORMATION FOR SEQ ID NO:12:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:12:

Arg Val thr Ile Arg Thr Val Arg Val Arg Arg Pro
1               5                       10

Pro   Lys   Gly   Lys   His   Arg   Lys
            15

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:13:

Gly   Lys   Lys   Arg   Ser   Lys   Ala
1                         5

( 2 ) INFORMATION FOR SEQ ID NO:14:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:14:

Lys   Ala   Lys   Arg   Ser   Lys   Ala
1                         5

( 2 ) INFORMATION FOR SEQ ID NO:15:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:15:

Asp   Arg   Leu   Arg   Arg
1                         5

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:16:

Pro   Lys   Gln   Lys   Arg   Lys
1                         5

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:17:

Val   Arg   Lys   Lys   Arg   Lys   Thr
1                         5

( 2 ) INFORMATION FOR SEQ ID NO:18:

( i ) SEQUENCE CHARACTERISTICS:
        ( A ) LENGTH: 7 amino acids
        ( B ) TYPE: amino acid
        ( C ) STRANDEDNESS: Not Relevant (D) TOPOLOGY: Not Relevant (xi) SEQUENCE DESCRIPTION: SEQ ID NO:18:

```
Ala    Lys    Lys    Ser    Lys    Gln    Glu
1                           5
```

(2) INFORMATION FOR SEQ ID NO:19:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (xi) SEQUENCE DESCRIPTION: SEQ ID NO:19:

```
Pro    Ala    Ala    Lys    Arg    Val    Lys    Leu    Asp
1                           5
```

(2) INFORMATION FOR SEQ ID NO:20:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (xi) SEQUENCE DESCRIPTION: SEQ ID NO:20:

```
Arg    Gln    Arg    Arg    Asn    Glu    Leu    Lys    Ser    Phe
1                           5                                  10
```

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (xi) SEQUENCE DESCRIPTION: SEQ ID NO:21:

```
Thr    Lys    Lys    Arg    Lys    Leu    Glu
1                           5
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (xi) SEQUENCE DESCRIPTION: SEQ ID NO:22:

```
Pro    Lys    Thr    Arg    Arg    Arg    Pro
1                           5
```

(2) INFORMATION FOR SEQ ID NO:23:

(i) SEQUENCE CHARACTERISTICS:
        (A) LENGTH: 7 amino acids
        (B) TYPE: amino acid
        (C) STRANDEDNESS: Not Relevant
        (D) TOPOLOGY: Not Relevant (xi) SEQUENCE DESCRIPTION: SEQ ID NO:23:

```
Ser    Gln    Arg    Lys    Arg    Pro    Pro
1                           5
```

(2) INFORMATION FOR SEQ ID NO:24:

( i ) SEQUENCE CHARACTERISTICS:
    ( A ) LENGTH: 12 amino acids
    ( B ) TYPE: amino acid
    ( C ) STRANDEDNESS: Not Relevant
    ( D ) TOPOLOGY: Not Relevant ( x i ) SEQUENCE DESCRIPTION: SEQ ID NO:24:

```
Arg  Leu  Pro  Val  Arg  Arg  Arg  Arg  Arg  Val  Pro
1              5                        10
```

( 2 ) INFORMATION FOR SEQ ID NO:25:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:25:

```
Gly  Arg  Lys  Lys  Arg
1              5
```

( 2 ) INFORMATION FOR SEQ ID NO:26:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:26:

```
Val  Arg  Thr  Thr  Lys  Gly  Lys  Arg  Lys  Arg  Ile  Asp
1              5                        10
Val
```

( 2 ) INFORMATION FOR SEQ ID NO:27:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:27:

```
Arg  Lys  Phe  Lys  Lys
1              5
```

( 2 ) INFORMATION FOR SEQ ID NO:28:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:28:

```
Arg  Arg  Asn  Arg  Arg  Arg  Arg  Trp
1              5
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:29:

```
Pro    Arg    Ser    Gly    Lys    Lys    Arg    Lys    Arg    Lys    Arg    Leu
1                           5                                  10
Lys    Pro    Thr
              15
```

( 2 ) INFORMATION FOR SEQ ID NO:30:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:30:

```
Lys    Lys    Lys    Lys    Lys
1                           5
```

( 2 ) INFORMATION FOR SEQ ID NO:31:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:31:

```
Pro    Pro    Lys    Lys    Arg
1                           5
```

( 2 ) INFORMATION FOR SEQ ID NO:32:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:32:

```
Pro    Lys    Lys    Lys    Lys    Lys
1                           5
```

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:33:

```
Ser    Lys    Arg    Val    Ala    Lys    Arg    Lys    Leu
1                           5
```

( 2 ) INFORMATION FOR SEQ ID NO:34:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:34:

```
Pro    Leu    Leu    Lys    Lys    Ile    Ile    Gln
1                           5
```

( 2 ) INFORMATION FOR SEQ ID NO:35:

( i ) SEQUENCE CHARACTERISTICS:

(A) LENGTH: 8 amino acids
(B) TYPE: amino acid
(C) STRANDEDNESS: Not Relevant
(D) TOPOLOGY: Not Relevant (xi) SEQUENCE DESCRIPTION: SEQ ID NO:35:

Pro Pro Gln Lys Lys Ile Lys Ser
1               5

(2) INFORMATION FOR SEQ ID NO:36:

(i) SEQUENCE CHARACTERISTICS:
(A) LENGTH: 7 amino acids
(B) TYPE: amino acid
(C) STRANDEDNESS: Not Relevant
(D) TOPOLOGY: Not Relevant (xi) SEQUENCE DESCRIPTION: SEQ ID NO:36:

Pro Gln Pro Lys Lys Lys Pro
1               5

(2) INFORMATION FOR SEQ ID NO: 37:

(i) SEQUENCE CHARACTERISTICS:
(A) LENGTH: 18 amino acids
(B) TYPE: amino acid
(c) STRANDNESS: n.a.
(D) TOPOLOGY: Not Relevant (xi) SEQUENCE DESCRIPTION: SEQ ID NO: 37:

Phe Lys Arg Lys His Lys Lys Asp Ile Ser Gln Asn
1               5                           10

Lys Arg Ala Val Arg Arg
        15

(2) INFORMATION FOR SEQ ID NO:38:

(i) SEQUENCE CHARACTERISTICS:
(A) LENGTH: 9 amino acids
(B) TYPE: amino acid
(C) STRANDEDNESS: Not Relevant
(D) TOPOLOGY: Not Relevant (xi) SEQUENCE DESCRIPTION: SEQ ID NO:38:

Ser Lys Cys Leu Gly Trp Leu Trp Gly
1               5

(2) INFORMATION FOR SEQ ID NO:39:

(i) SEQUENCE CHARACTERISTICS:
(A) LENGTH: 8 amino acids
(B) TYPE: amino acid
(C) STRANDEDNESS: Not Relevant
(D) TOPOLOGY: Not Relevant (xi) SEQUENCE DESCRIPTION: SEQ ID NO:39:

Gly Lys Arg Lys Asn Lys Pro Lys
1               5

(2) INFORMATION FOR SEQ ID NO:40:

(i) SEQUENCE CHARACTERISTICS:
(A) LENGTH: 7 amino acids
(B) TYPE: amino acid
(C) STRANDEDNESS: Not Relevant
(D) TOPOLOGY: Not Relevant (xi) SEQUENCE DESCRIPTION: SEQ ID NO:40:

```
Lys   Thr   Arg   Lys   His   Arg   Gly
1                       5
```

( 2 ) INFORMATION FOR SEQ ID NO:41:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:41:

```
Lys   His   Arg   Lys   His   Pro   Gly
1                       5
```

( 2 ) INFORMATION FOR SEQ ID NO:42:

( i ) SEQUENCE CHARACTERISTICS:
        ( A ) LENGTH: 18 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:42:

```
Arg   Arg   Leu   Ala   Gln   Asn   Arg   Glu   Ala   Ala   Arg   Lys
1                       5                             10

Ser   Arg   Leu   Arg   Lys   Lys
                  15
```

( 2 ) INFORMATION FOR SEQ ID NO:43:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:43:

```
Lys   Lys   Arg   Ala   Arg   Leu   Val   Arg   Asn   Arg   Glu   Ser
1                       5                             10

Ala   Gln   Leu   Ser
                  15
```

( 2 ) INFORMATION FOR SEQ ID NO:44:

( i ) SEQUENCE CHARACTERISTICS:
        ( A ) LENGTH: 5 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:44:

```
Arg   Gln   Arg   Lys   Lys
1                       5
```

( 2 ) INFORMATION FOR SEQ ID NO:45:

( i ) SEQUENCE CHARACTERISTICS:
        ( A ) LENGTH: 18 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:45:

```
Arg   Lys   Arg   Lys   Glu   Ser   Asn   Arg   Glu   Ser   Ala   Arg
1                       5                             10

Arg   Ser   Arg   Tyr   Arg   Lys
```

15

( 2 ) INFORMATION FOR SEQ ID NO:46:

( i ) SEQUENCE CHARACTERISTICS:
        ( A ) LENGTH: 13 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:46:

| Lys | Lys | Asn | Gln | Lys | His | Lys | Leu | Lys | Met | Lys | Arg |
| --- | --- | --- | --- | --- | --- | --- | --- | --- | --- | --- | --- |
| 1 | | | | 5 | | | | | 10 | | |

Lys ( 2 ) INFORMATION FOR SEQ ID NO:47:

( i ) SEQUENCE CHARACTERISTICS:
        ( A ) LENGTH: 18 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:47:

| Lys | Leu | Pro | Arg | Glu | Asp | Asp | Gly | Gln | Pro | Ser |
| --- | --- | --- | --- | --- | --- | --- | --- | --- | --- | --- |
| 1 | | | | 5 | | | | | 10 | |

| Glu | Arg | Lys | Arg | Glu | Arg |
| --- | --- | --- | --- | --- | --- |
| | | 15 | | | |

( 2 ) INFORMATION FOR SEQ ID NO:48:

( i ) SEQUENCE CHARACTERISTICS:
        ( A ) LENGTH: 17 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:48:

| Lys | Leu | Arg | Pro | Glu | Asp | Arg | Tyr | Ile | Gln | Thr | Glu |
| --- | --- | --- | --- | --- | --- | --- | --- | --- | --- | --- | --- |
| 1 | | | | 5 | | | | | 10 | | |

| Lys | Tyr | Gly | Arg | Arg |
| --- | --- | --- | --- | --- |
| | | 15 | | |

( 2 ) INFORMATION FOR SEQ ID NO:49:

( i ) SEQUENCE CHARACTERISTICS:
        ( A ) LENGTH: 15 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO:49:

| Lys | Thr | Lys | Tyr | Gly | Ser | Asp | Thr | Glu | Ile | Lys | Leu |
| --- | --- | --- | --- | --- | --- | --- | --- | --- | --- | --- | --- |
| 1 | | | | 5 | | | | | 10 | | |

| Leu | Ser | Lys |
| --- | --- | --- |
| | | 15 |

( 2 ) INFORMATION FOR SEQ ID NO: 50:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 50 :

| Met | Glu | Glu | Ala | Val | Thr | Met | Ala | Pro | Ala | Ala | Val |
|-----|-----|-----|-----|-----|-----|-----|-----|-----|-----|-----|-----|
| 1   |     |     |     | 5   |     |     |     |     | 10  |     |     |

| Ser | Ser | Ala | Val | Val | Gly | Asp | Pro |
|-----|-----|-----|-----|-----|-----|-----|-----|
|     |     | 15  |     |     |     |     | 20  |

(2) INFORMATION FOR SEQ ID NO: 51:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (xi) SEQUENCE DESCRIPTION: SEQ ID NO: 51:

| Met | Tyr | Asn | Ala | Ile | Leu | Arg | Arg | Lys | Leu | Glu | Glu |
|-----|-----|-----|-----|-----|-----|-----|-----|-----|-----|-----|-----|
| 1   |     |     |     | 5   |     |     |     |     | 10  |     |     |

| Asp | Leu | Glu |
|-----|-----|-----|
|     |     | 15  |

(2) INFORMATION FOR SEQ ID NO: 52:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (xi) SEQUENCE DESCRIPTION: SEQ ID NO: 52:

| Gly | Asp | Arg | Arg | Ala | Ala | Pro | Ala | Arg | Pro |
|-----|-----|-----|-----|-----|-----|-----|-----|-----|-----|
| 1   |     |     |     | 5   |     |     |     |     | 10  |

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: Not Relevant (xi) SEQUENCE DESCRIPTION: SEQ ID NO: 53:

| Met | Ser | Glu | Arg | Lys | Arg | Arg | Glu | Lys | Leu |
|-----|-----|-----|-----|-----|-----|-----|-----|-----|-----|
| 1   |     |     |     | 5   |     |     |     |     | 10  |

(2) INFORMATION FOR SEQ ID NO: 54:

(i) SEQUENCE CHARACTERISTICS:
        (A) LENGTH: 13 amino acids
        (B) TYPE: amino acid
        (C) STRANDEDNESS: Not Relevant
        (D) TOPOLOGY: Not Relevant (xi) SEQUENCE DESCRIPTION: SEQ ID NO: 54:

| Met | Ile | Ser | Glu | Ala | Leu | Arg | Lys | Ala | Ile | Gly | Lys |
|-----|-----|-----|-----|-----|-----|-----|-----|-----|-----|-----|-----|
| 1   |     |     |     | 5   |     |     |     |     | 10  |     |     |

Arg (2) INFORMATION FOR SEQ ID NO: 55:

(i) SEQUENCE CHARACTERISTICS:
        (A) LENGTH: 16 amino acids
        (B) TYPE: amino acid
        (C) STRANDEDNESS: Not Relevant
        (D) TOPOLOGY: Not Relevant (xi) SEQUENCE DESCRIPTION: SEQ ID NO: 55:

| Lys | Arg | Pro | Ala | Ala | Thr | Lys | Lys | Ala | Gly | Gln | Ala |
|-----|-----|-----|-----|-----|-----|-----|-----|-----|-----|-----|-----|
| 1   |     |     |     | 5   |     |     |     |     | 10  |     |     |

```
Lys     Lys     Lys Lys
                15
```

( 2 ) INFORMATION FOR SEQ ID NO: 56:

( i ) SEQUENCE CHARACTERISTICS:
        ( A ) LENGTH: 25 amino acids
        ( B ) TYPE: amino acid
        ( C ) STRANDEDNESS: Not Relevant
        ( D ) TOPOLOGY: Not Relevant ( x i ) SEQUENCE DESCRIPTION: SEQ ID NO: 56:

```
Pro     Lys     Lys     Lys     Arg     Lys     Val     Ser     Gly     Gly     Gly     Gly
1                               5                                               10
Gly     Lys     Lys     Lys     Lys     Lys     Lys     Lys     Lys     Lys     Lys     Lys
                15                                      20
Lys
25
```